United States Patent
Elss et al.

(10) Patent No.: US 11,308,660 B2
(45) Date of Patent: Apr. 19, 2022

(54) MOTION COMPENSATED CARDIAC VALVE RECONSTRUCTION

(71) Applicant: KONINKLIJKE PHILIPS N.V., Eindhoven (NL)

(72) Inventors: Tanja Elss, Hamburg (DE); Michael Grass, Hamburg (DE); Rolf Dieter Bippus, Hamburg (DE); Axel Thran, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 255 days.

(21) Appl. No.: 16/633,843

(22) PCT Filed: Jul. 23, 2018

(86) PCT No.: PCT/EP2018/069862
§ 371 (c)(1),
(2) Date: Jan. 24, 2020

(87) PCT Pub. No.: WO2019/020541
PCT Pub. Date: Jan. 31, 2019

(65) Prior Publication Data
US 2021/0150778 A1   May 20, 2021

(30) Foreign Application Priority Data
Jul. 27, 2017   (EP) ..................... 17183539

(51) Int. Cl.
*G06T 11/00*   (2006.01)
*A61B 6/03*   (2006.01)
*A61B 6/00*   (2006.01)

(52) U.S. Cl.
CPC ............ *G06T 11/005* (2013.01); *A61B 6/032* (2013.01); *A61B 6/503* (2013.01); *A61B 6/5264* (2013.01); *A61B 6/5288* (2013.01); *G06T 2210/41* (2013.01)

(58) Field of Classification Search
CPC ... G06T 11/005; G06T 2210/41; A61B 6/032; A61B 6/503; A61B 6/5264; A61B 6/5288; A61B 6/486; A61B 6/5205
See application file for complete search history.

(56) References Cited

U.S. PATENT DOCUMENTS

2001/0045856 A1   11/2001   Ooishi
2007/0110294 A1   5/2007   Schaap
(Continued)

FOREIGN PATENT DOCUMENTS

EP   2357613 A2 *   8/2011   .......... G06T 11/005
EP   2176684 B1   4/2015
(Continued)

OTHER PUBLICATIONS

PCT International Search Report, International application No. PCT/EP2018/069862, dated Sep. 3, 2018.
(Continued)

*Primary Examiner* — Courtney D Thomas
(74) *Attorney, Agent, or Firm* — Larry Liberchuk

(57) ABSTRACT

Motion compensated reconstruction is currently not well-suited for reconstructing the valve, the valve leaflets and the neighboring vascular anatomy of the heart. Blurring of the valve and the valve leaflets occurs. This may lead to wrong diagnosis. A new approach for motion compensated reconstruction of the valve and the related anatomy is presented in which an edge-enhancing step is performed to suppress blurring.

14 Claims, 4 Drawing Sheets

(56) References Cited

U.S. PATENT DOCUMENTS

| | | |
|---|---|---|
| 2008/0181479 A1 | 7/2008 | Yang |
| 2009/0238412 A1 | 9/2009 | Grass |
| 2010/0025589 A1 | 2/2010 | Olcott |
| 2013/0077843 A1 | 3/2013 | Bruder |
| 2016/0256127 A1 | 9/2016 | Lee |

FOREIGN PATENT DOCUMENTS

| | | | |
|---|---|---|---|
| WO | WO2005008597 A2 | 1/2005 | |
| WO | WO2008149359 A2 | 12/2008 | |
| WO | WO2008155680 A2 | 12/2008 | |
| WO | WO2009050619 A2 | 4/2009 | |

OTHER PUBLICATIONS

Schafer, D. et al., "Motion Compensated Cone Beam Filtered Back-Projection for 3D Rotational X-Ray Angiography: A Simulation Study", Proceedings of the 8th International Meeting on Fully Three-Dimensional Image Reconstruction, Aug. 2005, pp. 360-363, XP002479628.

Kabus S. et al., "Fast Elastic Image Registration." Proceeding of Medical Image Analysis for the Clinic: A Grand Challenge, MICCAI, pp. 81-89, 2010.

Schafer D. et al., "Motion-Compensated and Gated Cone Beam Filtered Back-Projection for 3-D Rotational X-Ray Angiography", IEEE Transactions on Medical Imaging, vol. 25, No. 7, pp. 898-906, Jul. 2006.

Isola A. et al., "Fully Automatic Non-Rigid Registration-Based Local Motion Estimation for Motion-Corrected Iterative Cardiac CT Reconstruction", Medical Physics, vol. 37, No. 3, pp. 1093-1109, 2010.

Dowsey et al., "Motion-Compensated MR Valve Imaging with COMB Tag Tracking and Super-Resolution Enhancement", Med Image Comput Comput Assist Interv. (MICCAI), vol. 4191, pp. 364-371, 2006.

Bousse A. et al., "Motion Compensated Tomography Reconstruction of Coronary Arteries in Rotational Angiography", IEEE Transactions on Biomedical Engineering, vol. 56, issue 4, pp. 1254-1257, Apr. 2009.

* cited by examiner

MOTION COMPENSATED CARDIAC VALVE RECONSTRUCTION

FIELD OF THE INVENTION

The present invention relates to the field of digital imaging, more particularly to computed tomography (CT) imaging. In particular, the present invention relates to a method of reconstructing an image of an object from projection data of said object, an image processing device for reconstructing said image, a computer program for reconstructing the image and a computer readable medium.

BACKGROUND OF THE INVENTION

Computed tomography (CT) is a process of using digital processing to generate a three-dimensional image of an object of interest from a series of two-dimensional X-ray images collected around an axis of rotation. Such CT images may subsequently be reconstructed using appropriate algorithms.

An important application of computed tomography is cardiac computed tomography, in which the heart of a patient is the object of interest. A major issue with cardiac computed tomography stems from the fact that the heart is beating during image collection. Such motion decreases the quality of the images collected.

In order to mitigate this problem, cardiac CT typically employs a gated reconstruction, in which the cardiac CT data acquisition is performed in parallel with acquisition of data providing information over the cardiac cycle, such as electrocardiogram (ECG) or photoplethysmographic (PPG) data. This data is hereby used to gate the CT image acquisition and reconstruction by means of respectively selected phase points of the cardiac cycle.

WO 2005/008597 discloses a method for motion compensated reconstruction of cardiac CT images, wherein a motion of the object of interest in a selected region is estimated. On the basis of the estimated motion, time points are determined at which the selected regions have minimal motion. An image is subsequently reconstructed with the data for which the respective regions are reconstructed corresponds to the respective time points at which the regions have minimal motion.

So far, motion compensated cardiac CT reconstruction has been focused on motion compensation of the coronary arteries. However, in the past years, the diagnosis and treatment planning of valvular diseases has become a further field of interest in cardiac CT. When imaging the valve, the problem of blurring of the valve, the valve leaflets and the neighboring vascular anatomy due to motion arises. The previous approach for removing motion artifacts is not sufficient to suppress this blurring. Accordingly, determination of the valve, the valve leaflets and the neighboring vascular anatomy is not ideal, due to the motion thereof. In diagnosis and treatment planning, this may lead to wrong device sizing or incorrect estimation of calcifications.

SUMMARY OF THE INVENTION

It is an object of the present invention to provide an improved method for motion compensated reconstruction of volumetric data of an object of interest. It is a further object of the present invention to provide a method for motion compensated reconstruction of CT data for diagnosis and treatment planning of valvular diseases, by enabling the reduction of motion artifacts caused by movement of the valve and the valve leaflets. More particularly, it is an object of the present invention to provide a method for motion compensated reconstructions in which the blurring caused by movement of the valve and the valve leaflets may be suppressed.

The object of the present invention is solved by a method for reconstructing an image of an object of interest according to the invention, a respective image processing device, a computer program and a computer readable medium, as defined by the claims.

According to a first aspect of the invention, a method for reconstructing an image of an object of interest from a plurality of projection data of said object corresponding to a plurality of time points is provided. The method comprises the steps of retrieving a plurality of volumetric data of the object of interest from the plurality of projection data, each one of the volumetric data corresponding to a respective time point, and applying a gradient-based filter on the plurality of volumetric data to obtain a plurality of edge-enhanced image volumes corresponding to the respective time points. The method further comprises the steps of weighting of the plurality of edge-enhanced image volumes, estimating a plurality of first motion vector fields on the basis of the plurality of edge-enhanced image volumes and reconstructing a plurality of first motion compensated image volumes from the plurality of projection data using the estimated plurality of first motion vector fields, each of the plurality of first motion compensated image volumes corresponding to a respective time point.

In accordance with the invention, a gated multi-phase reconstruction is used. However, in contrast to known approaches, instead of performing registration and motion compensated reconstruction on the volumetric data directly, the registration and motion compensated reconstruction is performed on an edge-enhanced image volume, which is the result of a gradient-based filter operation that enhances the edges detected for the image of interest.

The volumetric data is hereby retrieved from a plurality of projection data that correspond to a plurality of time points. Accordingly, each of the volumetric data likewise corresponds to a respective time point, namely the time point corresponding to the projection data that has been used to obtain the volumetric data.

In this context, it should be mentioned that the term "time point" is not limited to being an actual "point in time", but may also relate to a particular time period or a phase point, for example of the cyclic motion of the heart, and/or a corresponding temporal window for each phase point. Alternatively or additionally, the term "time point" may also relate to an average of the acquisition times at which the respective projections belonging to the projection data for an image have been acquired.

Thus, there is one volumetric data for each particular time point. This volumetric data is filtered with a gradient-based filter. Such a gradient-based filter operation means that the gradients and the gradient magnitude for each data point of the volumetric data are determined. Edges in the volumetric data represent a strong increase or decrease, which is represented by a large gradient magnitude. Accordingly, by applying a filter that filters data points for which the gradient magnitude does not reach a particular threshold, produces an image volume in which the edges are enhanced, since it can be assumed that the larger gradient magnitudes represent edges.

Subsequently, a registration of the edge-enhanced images is performed to estimate a plurality of motion vector fields. In such a registration, one of the plurality of edge-enhanced image volumes corresponding to one particular time point is used as a reference image volume. Thus, one particular time point is selected as a reference time point.

Advantageously, the registration procedure is then performed by means of an elastic registration. The elastic registration procedure follows a volumetric registration approach, i.e. there is no extraction of certain reference points from the reference image volume, but rather the entire voxel information of the reference image volume is used for registration purposes. Thus, by comparing the entire voxel information of the reference image volume to each of the remaining edge-enhanced image volumes, a plurality of first motion vector fields from the reference image volume at the reference time point to the remaining edge-enhanced image volumes of the remaining time points can be estimated. This elastic registration approach is described in detail in "S. Kabus et al., Fast elastic image registration, Proc. of the Medical Image Analysis For The Clinic—A grand challenge, MICCAI, pp. 81-89, 2010", the entirety of which is hereby incorporated herein by reference.

Alternatively, a landmark based registration procedure could be performed, in which, in the reference image volume, particular reference regions or reference points are determined. Then, the same reference regions or reference points are determined in the remaining edge-enhanced image volumes for the remaining time points. The plurality of first motion vector fields is determined from the reference image volume at the reference time point to the remaining edge-enhanced image volumes of the remaining time points on the basis of these reference points.

These motion vector fields are used to perform a motion compensated filtered back projection using the projection data. The result of this motion compensated filtered back projection is an improved image, in which the blurred edges have been accounted for.

According to one embodiment, the object of interest comprises the valves and the valve leaflets, and the projection data comprises cardiac computed tomography (CT) projection data obtained together with one or more of simultaneously measured electrocardiogram (ECG) data or photoplethysmographic (PPG) data.

Typically, the valve and the valve leaflets are assessed using ECG or PPG-gated cardiac computed tomography (CT). Thus, ECG or PPG-data is used to track the cardiac cycle. Collection of CT projection data is only performed for particular time points that correspond to particular phases of the cardiac cycle. For investigation of the valve, the phases for 20%, 25%, 30%, 35% and 40% cardiac cycle may advantageously be used, i.e. the phases around the phase in which the aortic valve is opened (30%). Alternatively or additionally, phases for 60%, 65%, 70%, 75% and 80% cardiac can be used, which corresponds to the phases around the phase in which the aortic valve is closed (70%).

The CT projection data collected for the particular time point, i.e. the particular phase may hereby be collected by helical or circular CT using a cone beam. However, it is clear that the projection data may also be obtained by means other than computed tomography, such as X-ray imaging or magnetic resonance imaging, as long as it allows for determining the object of interest at different time points.

According to a further embodiment, the time points are determined on the basis of, for example, ECG or PPG data whereby the time points correspond to a cardiac phase of the heart.

According to an embodiment, the applying a gradient-based filter on the plurality of volumetric data comprises the steps of obtaining a noise-reduced image volume from the volumetric data by applying a smoothing filter, determining a gradient and/or gradient magnitude for each of the data points of the noise-reduced image volume, determining a plurality of local maxima of the gradient magnitude for each of the data points and suppressing the data points that do not correspond to said local maxima. The method further comprises the steps of determining a first threshold value for the gradient magnitude and a second threshold value for the gradient magnitude, the first threshold value being smaller than the second threshold value, determining, for each data point, whether the gradient magnitude is below or above the second threshold value and determining, for each data point, whether the gradient magnitude is below or above the first threshold value. The method further comprises marking a set of data points for which the gradient magnitude is above the first threshold value and which are connected to data points for which the gradient magnitude is above the second threshold value and obtaining, from the marked set of data points, the edge enhanced image volume.

The gradient-based filter operation may be performed in multiple steps, whereby each step is performed on each of the volumetric data.

In a first step, a noise reduction is performed on the volumetric data. In medical imaging, the data typically picks up noise from a variety of sources. This noise needs to be removed to obtain an improved image. Since a significant amount of noise stems from Gaussian noise, noise removal for the volumetric data may advantageously be done by applying a Gaussian filter. This results in a smoothed image volume. Alternatively, a moving average filter or other kinds of filters may be applied that are suitable for reducing the noise and smoothing the image volume.

According to an embodiment, the obtaining of the smoothed image volume is achieved by applying a Gaussian filter on the volumetric data.

In a second step, a gradient and a gradient magnitude may be determined for each data point of the smoothed image. In this context, it shall be understood that the data points of the smoothed image represent the data points of the volumetric data, which have been corrected for noise. The gradient for each data point has to be determined each direction of the projection data. The partial derivatives in the respective directions may hereby be determined in a variety of ways. For example, a central differences method may be used to approximate, for example a first partial derivative ($G_x$) in the vertical direction, and a second and third partial derivative ($G_y$, $G_z$) in the y and z direction. These derivatives determine the gradient of the respective data point. Further, the partial derivatives allow for determining the gradient magnitude. The gradient magnitude for each pixel is hereby calculated by determining the Euclidean norm of the partial derivative in vertical, y and z-direction according to $$G=\sqrt{G_x^2+G_y^2+G_z^2}$$

Thus, in a further embodiment, the determining the gradient for each of the data points is performed using central differences and the determining for the gradient magnitude for each of the data points of the smoothed image volume is performed using the Euclidean norm. The present invention is, however, not limited to using central differences and the Euclidean norm.

The gradient may also be determined by convolution with an edge detection operator, such as a Sobel operator or a Roberts or Prewitt operator or the like. Further, the gradient magnitude may be determined using other norms like the maximum norm or p-norm.

In a third step, a non-maximum suppression is performed. That means that a plurality of local maxima is determined for the gradient magnitudes for each one of the data points. Thus, a gradient magnitude for particular data point is compared to the gradient magnitude of the neighboring data points. These neighboring data points can be aligned left and right of the supposed edge or may be regarded along the gradient. In case one of the compared gradient magnitude values is higher, the value of the particular data point is set to zero. Else, it will remain non-zero. Thus, the data points that do not correspond to local maxima are all set to zero.

In a further step, hysteresis thresholding is performed to determine which data points actually belong to an edge. Hereby, a first suitable threshold value $T_1$ and a second suitable threshold value $T_2$ are determined for the gradient magnitude (value) of each data point, whereby $T_2$ is larger than $T_1$. The gradient magnitude (value) of the data points of the gradient-based image volume is then compared to the second threshold value $T_2$. This may, for example, be performed by means of a first binary mask being applied to the gradient-based image volume. This first binary mask determines each data point for which the gradient magnitude has a value above the second threshold value $T_2$ and these data points are set to "True" for the first binary mask.

Then, the gradient magnitude of the data points of the gradient-based image volume is compared to the first threshold value $T_1$. This may be embodied, for example, by applying a second binary mask to the gradient-based image volume, which determines each data point for which the gradient magnitude is above the first threshold value $T_1$ and which sets these data points to "True" for the second binary mask.

Subsequently, it is started from the data points that are above the second threshold value $T_2$. These data points are then dilated, i.e. the connected data points surrounding these data points are considered with respect to their gradient magnitude. In the context of this application, these data points are considered to be connected to the data points that are above the second threshold value. When considering the connected data points, the first threshold value $T_1$ is used as a lower limit. The adjacent data points having a gradient magnitude below the threshold value $T_1$ are therefore disregarded and the adjacent data points having a gradient magnitude above the first threshold value are maintained and marked as belonging to the edge.

This approach may, for example, be employed by performing reconstruction by dilation, i.e. by dilating the first binary mask for determining the data points having a gradient magnitude above the second threshold value with a 3*3*3 cube until the dilation is limited by the second mask representing the first threshold value. The set of data points maintained during this dilation procedure is then considered as belonging to an edge. Thus, as a result of this hysteresis thresholding, the edge-enhanced image volume is provided.

According to a further embodiment the determining the gradient and/or the gradient magnitude for each of the data points further includes determining a direction of the gradient.

In addition to determining the gradient and the gradient magnitude, it may be advantageous to also determine the direction of the gradient. Knowledge about the direction of the gradients may be used to avoid miss-registration during the registration procedure. The direction of the gradient may be determined by known measures, for example by adapting the similarity measure of the registration procedure accordingly.

In a further embodiment, the obtaining of the edge-enhanced image volume further comprises determining a normalized gradient magnitude and weighting the marked data points using the normalized gradient magnitude.

After non-maximum suppression and hysteresis thresholding, the edge-enhanced image volume only contains data points that are considered as belonging to edges. These marked data points may further be weighted according to the normalized gradient magnitude prior to being subjected to the registration and motion compensated reconstruction procedure. The gradient magnitude may hereby be normalized according to known methods. Then, the hysteresis result is weighted with said normalized gradient magnitude. Data points that have been marked as not being "True" during the above-described hysteresis thresholding are hereby set to a value of zero, whereas data points that have been marked as being "True" are mapped to values within the range of [0.5; 1]. The actual value that is obtained for the gradient magnitude depends on a predefined normalization window.

According to an even further embodiment the estimation of the plurality of motion vector fields comprises determining a first one of the plurality of edge-enhanced image volumes as a first reference image volume, and estimating the plurality of first motion vector fields from the first reference image volume to the remaining ones of the plurality of edge-enhanced image volumes using the first reference image volume.

The estimation of motion vector fields is performed according to known methods. Accordingly, one edge-enhanced image volume from the plurality of edge-enhanced image volumes corresponding to one particular time point is selected as reference image volume. Advantageously, the registration procedure is performed by means of an elastic registration as described herein above. Alternatively, a landmark-based registration procedure could be used.

The motion of the object as determined during registration is described by a respective motion vector field from the reference point in the reference image volume to the reference point in the respective further edge-enhanced image volume. Accordingly, for each edge-enhanced image volume that is not the reference image volume, a motion vector field may determine the displacement of a respective voxel of the edge-enhanced image volume for the respective time difference between the reference time point and the time point of the edge-enhanced image volume that is not the reference image volume. Advantageously, the thus obtained motion vector fields are then interpolated in the time domain as described e.g. in "D. Schafer et al., Motion compensated and gated cone beam filtered back-projection for 3D rotational angiography, IEEE Transactions on Medical Imaging, vol. 25, no. 7, pp 898-906, 2006". By means of an interpolation in the time domain the temporal projection range that is required for the reconstruction can be covered. Since the motion vector field describes the motion of the object, it enables a motion compensation and, thus, a motion compensated back projection for image reconstruction.

In the particular case where the object of interest comprises the valve and the valve leaflets, the reference time points are advantageously selected to be at about 30% cardiac cycle (aortic valve opened) or at about 70% cardiac cycle (aortic valve closed). The volumetric data obtained for these phases may be subjected to the gradient-based filter operation and then used as a reference image volume for estimating the motion vector fields. Hereby, the motion vector fields may advantageously be determined for edge-enhanced image volumes derived from volumetric data obtained at 20%, 25%, 35% and 40% cardiac phase for the reference time point being at 30% cardiac phase and for edge-enhanced image volumes derived from volumetric data obtained at 60%, 65%, 75% and 80% cardiac phase for the reference time point being at 70% cardiac phase.

In accordance with a further embodiment, a sequential processing of the image volumes of the object of interest is performed by performing a second pass motion compensation on the first motion compensated image volumes which takes the movement of the valve leaflets into account.

In a further embodiment, the method for reconstructing further comprises the steps of obtaining a plurality of line filtered image volumes from the plurality of first motion compensated image volumes and estimating a plurality of second motion vector fields on the basis of the plurality of line filtered image volumes. The method also comprises the step of reconstructing a plurality of second motion compensated images of the object from the plurality of line filtered image volumes using the estimated plurality of second motion vector fields.

The second pass motion compensation is hereby performed in a similar manner as the first pass motion compensation. Accordingly, each motion compensated image volume of the plurality of motion compensated image volumes corresponding to a particular time point is filtered. The filtered results are subsequently registered to a reference and a motion compensated reconstruction is performed. However, instead of a gradient-based edge filter, a line filtering technique is used. While the valves are typically visible through edges in volumetric images, the valve leaflets are often represented by a plane shape in volumetric images and by small lines along the gradient direction. Thus, the line filtering technique is more sensible to the valve leaflets. Advantageously, the line filtering technique used enhances dark structures from a bright background. This may be achieved, for example, by a black top-hat transform as a filter operation. Further, the line filtering may be performed by means of a convolution using a respective line detection operator. Alternatively, other line filtering techniques may also be employed. The result of the line filtering of the first motion compensated image volumes are respective line filtered image volumes, whereby each of the line filtered image volumes corresponds to a particular point in time. This point in time corresponds to the point in time for the first motion compensated image volumes.

These line filtered image volumes are then used for the estimation of a plurality of second motion vector fields. Hereby, a particular one of the line filtered image volumes for a particular time point is selected as a second reference image volume. Advantageously, the registration procedure is performed employing elastic registration on the remaining image volumes as a whole, i.e. by the volumetric approach of considering the entire voxel information of the image volumes, instead of determining a subset of features in the image volumes, such as reference points or reference areas. On the basis of this approach, second motion vector fields from the second reference image volume to the remaining ones of the plurality of line filtered image volumes are then estimated. Alternatively, other registration techniques including a landmark-based registration procedure, in which respective reference points or reference regions are determined in the second reference image volume and the second motion vector fields are determined using these reference points may also be employed. Based on these second motion vector fields, a motion compensated filtered back projection is performed, resulting in a plurality of second motion compensated images of the object. To this end, the plurality of second motion compensated images of the object may also be a single second motion compensated image, in particular the second motion compensated image corresponding to the time point that was selected as a reference time point.

Advantageously, the second reference image volume of the second pass may be selected for the same reference time point as the reference image volume for the first pass, for example the time point at 30% cardiac phase or 70% cardiac phase. The remaining line filtered image volumes for the second pass may also be selected as corresponding to the remaining time points selected in the first pass, for the references at 30% and 70%, respectively, i.e. selected at temporal distances corresponding to 5% cardiac cycle each. Even more advantageously, smaller temporal distances may be used, such as time points for each 1% cardiac cycle.

According to a further embodiment, the obtaining the plurality of line filtered image volumes comprises determining a registration transformation for registering a first one of the first motion compensated image volumes to each of the remaining ones of the plurality of first motion compensated image volumes and obtaining the plurality of line filtered image volumes from the plurality of registered first motion compensated image volumes.

In the first pass motion compensation, the blurring of the edges of the valve has been reduced. Thus, the contours on the first motion compensated image volumes may be sharper. Despite this, there is still a chance that they are also strongly shifted during the cardiac cycle. Thus, in order to properly determine motion of the valve leaflets, the leaflet motion has to be distinguished from the overall motion. In order to achieve this, a 3D to 3D registration of the first motion compensated image volumes is performed to determine a potential shifting of the edges during the cardiac cycle.

This is done by selecting a 3D reference image volume and determining respective reference points in the 3D reference image volume. These reference points may advantageously comprise the edges or contours of the valves and ventricles of the heart. Subsequently, the respective points are determined for the remaining first motion compensated image volumes and respective transformation vector fields from the 3D reference image volume to the remaining first motion compensated image volumes are determined. These registered first motion compensated image volumes may then be subjected to the second pass motion compensation.

In a further embodiment the method comprises a selection of a region of interest within the volumetric data.

It may be advantageous that the area for which motion compensation shall be performed is selected for both, the first pass motion compensation and the second pass motion compensation. Accordingly, a region of interest may be determined.

In a computer-based approach, this determination may be performed either automatically by the heart segmentation or by an active user interaction. One practical approach of determining a region of interest may hereby be realized using an image processing device and a respective user interface. This user interface may include respective masks for the particular regions of interest. More particularly, a mask may be provided that can be used when the motion of the valves shall be compensated and a further mask may be provided for (second pass) compensation of the valve leaflets.

Thus, according to a further aspect of the invention, an image processing device for reconstructing an image of an object of interest from a plurality of projection data of said object corresponding to a plurality of time points is provided. The image processing device comprises a memory adapted to store a plurality of volumetric data of the object of interest retrieved from the plurality of projection data, each volumetric data corresponding to a respective time point and a filtering unit adapted to apply a gradient-based filter on the plurality of volumetric data to obtain a plurality of edge-enhanced image volumes corresponding to the respective time points. The image processing device further comprises a determination unit adapted to estimate a plurality of first motion vector fields on the basis of the plurality of edge-enhanced image volumes and a reconstruction unit adapted to reconstruct a plurality of first motion compensated image volumes of the object from the projection data using the estimated plurality of first motion vector fields, each of the plurality of first motion compensated image volumes corresponding to a respective time point.

According to an even further aspect, a computer program is provided. The computer program comprises program code means, which when executed by a processing unit, cause the image processing device to perform the method according to the invention. In a further aspect, a computer-readable medium having stored thereon the computer program is provided.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
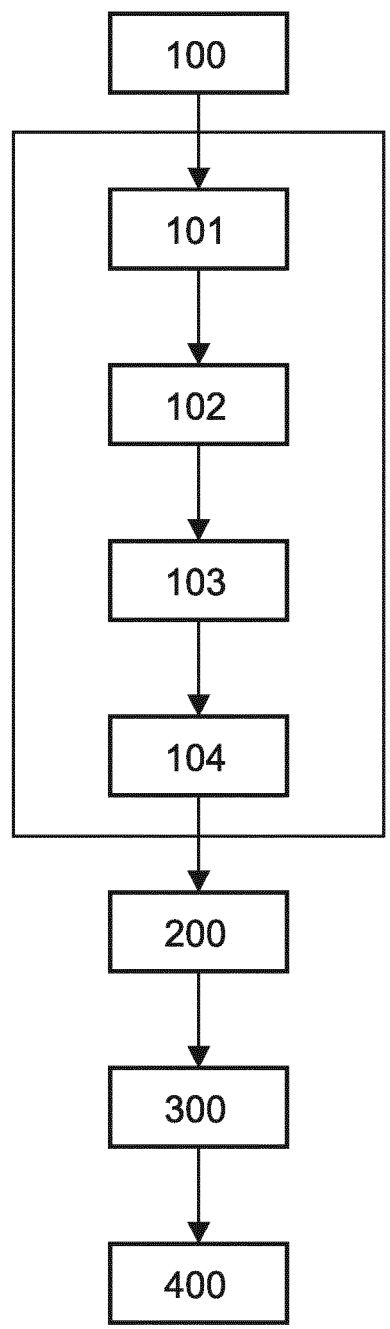
FIG. 1 schematically illustrates an embodiment of a method for motion compensated reconstruction according to the invention.

The illustration in the drawings is schematically. In different drawings, similar or identical elements are provided with the same reference numerals.

FIG. 1 represents schematically an embodiment of a method for first pass motion compensated reconstruction of an object of interest from volumetric data including projection data. In this particular embodiment, the volumetric data comprises cardiac CT projection data and ECG data. The object of interest is the heart of a patient, including the valve and the valve leaflets.

In the present embodiment, the reconstruction is performed for time points corresponding to 20%, 25%, 30%, 35% and 40% cardiac phase, whereby the time point corresponding to 30% cardiac phase corresponds to the reference time point for registration and the volumetric data for that time point corresponds to the reference image volume.

The method starts at step 100 with performing a conventional cardiac CT scan in helical acquisition mode, resulting in an acquisition of projection data. At the same time, electrocardiogram (ECG) data is also acquired.

The projection data and the ECG data are hereby simultaneously retrieved for each time point corresponding to the cardiac phases between 20% to 40% with a 5% distance for each phase. Then, the volumetric data is obtained for the respective different time points from the projection data.

Each volumetric data is then subjected to a noise reduction by means of a filter operation is step 101. In the embodiment according to FIG. 1, a Gaussian filter is applied to the volumetric data. This produces a smoothed image volume in which smaller structures are no longer present. Accordingly, by means of this Gaussian filter, the noise effects on the edges are reduced.

In step 102, the smoothed image volume is used for edge detection. In the present embodiment, the central differences method is used to determine a value for the partial derivatives in all directions. This allows for determining the gradient magnitude for each image data point of the smoothed image volume derived from the volumetric data by determining the Euclidean norm of the partial derivative in each direction according to $$G=\sqrt{\Sigma G_i^2}$$

Thus, respective edge-enhanced image volumes representing the gradient magnitudes are generated for each time point. The data points for which the gradient magnitudes have the highest value are assumed to correspond to the regions of the volumetric data in which the change in brightness is the largest, i.e. the regions of the edges.

In step 103, edge thinning is performed by applying a non-maximum suppression procedure. In non-maximum suppression, the value for the gradient magnitude of one data point of the edge-enhanced image is compared with that of the respective data points in the positive and negative gradient directions. If the value of the gradient magnitude of the current data point is higher compared to that in the positive or negative gradient direction, its value will be preserved, else it will be set to zero. Accordingly, all values for each of the data points except for the local maxima are suppressed, such that the edge is only represented by the data points having the highest value of gradient magnitude. This process thus results in a sharpening of the edges.

Edge-thinning by non-maximum suppression provides an edge-enhanced image that comprises a more accurate representation of the edges within the volumetric data. However, due to noise or other disturbing features, there may still be some data points left for which the value of gradient magnitude has not yet been set to zero despite the data point not actually corresponding to an edge.

In order to compensate for this, in step 104, a hysteresis thresholding is performed. For this hysteresis thresholding, two threshold values $T_1$ and $T_2$ are defined, whereby $T_1$ is smaller than $T_2$. A first binary mask is then used on the gradient-based image volume. By means of this binary mask, the gradient magnitude of the data points of the gradient-based image volume is compared to the second threshold value $T_2$. Each data point for which the gradient magnitude is above the second threshold value $T_2$ is set to "True" for the first binary mask.

Subsequently, a second binary mask is used to compare the gradient magnitude of the data points of the gradient-based image volume to the first threshold value $T_1$ to determine those data points for which the gradient magnitude is above the first threshold value $T_1$. These data points are then set to "True" for the second binary mask.

In the following, a reconstruction by dilation is performed. Thus, the data points above the second threshold value, i.e. the data points that are "True" for the first binary mask, are used as starting points. The first binary mask is then dilated with a 3×3×3 cube using the second binary mask as a limit. Thus, the dilation of the mask causes the data points adjacent to the starting points to be considered in that the connected data points having a gradient magnitude below the first threshold value $T_1$ are disregarded and the adjacent data points having a gradient magnitude above the first threshold $T_1$ value are considered as belonging to the edge.

The filtering process is performed for the volumetric data collected at each time point. Thus, the output of this filtering process according to step 100 is a plurality of edge-enhanced image volumes, each comprising a filtered set of data points representing edges of the volumetric data collected for each time point corresponding to a respective cardiac phase.

In step 200, the normalized gradient magnitude is determined. Each one of the edge-enhanced image volumes is then subjected to a weighting operation, in which the edges are weighted with said normalized gradient magnitude. Accordingly, the output of step 200 is a plurality of normalized edge-enhanced image volumes.

In step 300, the plurality of normalized edge-enhanced image volumes that have been derived from the volumetric data for the different time points are subjected to a registration procedure. Hereby, the normalized edge-enhanced image volume as determined for 30% cardiac phase is used as the reference image volume. Registration is performed by comparing the entire voxel information of the reference image volume for 30% cardiac phase to the entire voxel information in each of the remaining normalized edge-enhanced image volumes for the other cardiac phases. Subsequently, the motion vector fields from the reference image volume to the remaining normalized edge-enhanced image volumes are estimated by calculating the displacement vectors from the normalized edge-enhanced image volume selected as the reference image volume at the reference time point to each of the normalized edge-enhanced image volumes for the time points corresponding to 20%, 25%, 35% and 40% cardiac phase.

In step 400, the motion vector fields are used for motion compensated reconstruction. More particularly, the motion vector fields from the reference edge-enhanced image volume to the edge-enhanced image volumes for a particular time point corresponding to a particular cardiac phase are used to compensate for the motion in the reconstruction of the projection data for that particular phase. Since the blurring of the valve as a part of the object of interest has already been accounted for by means of the edge detection, the motion compensation reconstruction based on the projection data and the first motion vector fields determined using the edge-enhanced image volumes leads to an improved image of the object of interest, i.e. the heart.

Figure 2:
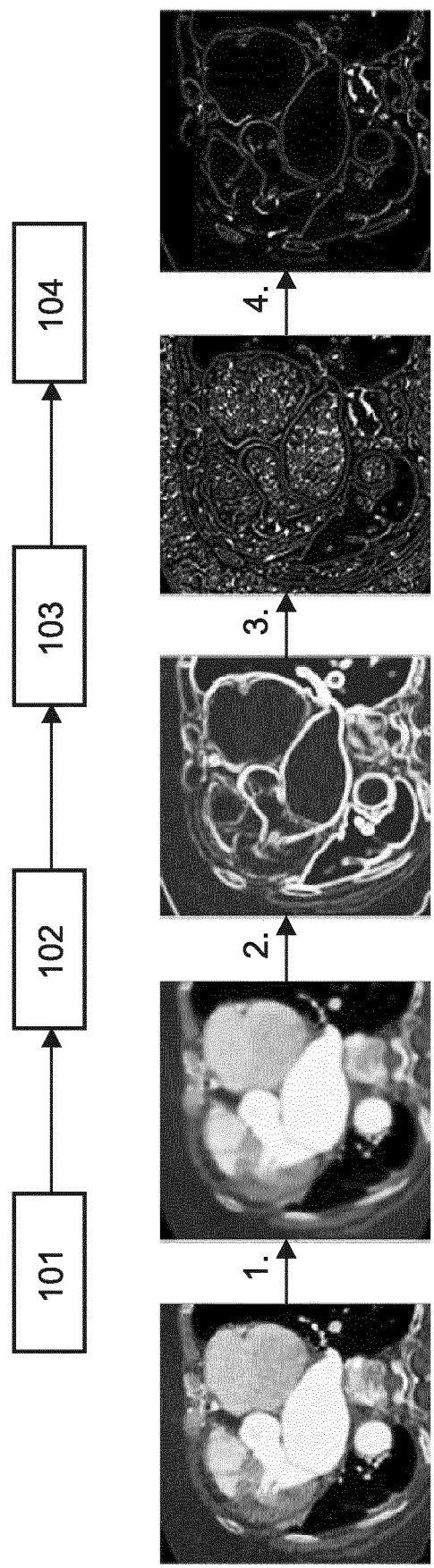
FIG. 2 shows a representation of volumetric data when subjected to a gradient-based filter operation according to the invention to retrieve an edge enhanced image.

FIG. 2 shows one axial slices of the volumetric CT image data when subjected to a gradient-based filter operation according to the invention to retrieve an edge enhanced image.

Hereby, the respective steps of the filtering operation are represented between the two image volumes that correspond to the input and the output of the particular step from left to right. First, volumetric data retrieved from CT projection data is received. In the present embodiment, the data corresponds to a gated cardiac CT image on which level contrast enhancement has been performed. This gated cardiac CT image is represented as the first image when going from left to right. In step 101, a Gaussian filter is applied on the CT image to reduce noise. The filtering results in the second image of the row of images. As may clearly be appreciated from the representation, the second image is smoothed compared to the first image.

In step 102, the gradient and gradient magnitude are calculated. The third image thus shows a gradient-based image volume that represents the gradient magnitude at the different data points of the image. Thus, at this stage, the gradient magnitude for substantially each data point is greater equal zero ($\geq 0$).

In step 103, the data points representing local maxima of the gradient magnitudes are determined and represented. The data points for which the gradient magnitude does not represent a local maximum are set to zero (i.e. suppressed). This results the fourth image, in which the data points are shown in a more discrete manner. That is, the data points in the fourth image either have a large gradient magnitude or are set to zero. As may be appreciated from the fourth image volume, there are still a rather large number of data points left that do not seem to belong to edges, but rather relate to other occurrences causing a large gradient magnitude.

Thus, in step 104, hysteresis thresholding is applied. Hereby, a suitable first and a second threshold value are determined, with the second threshold value being larger than the first threshold value. Then, a first binary mask is used on the gradient-based image volume, to detect all data points for which the gradient magnitude has a value above the second threshold value. Then, a second binary mask is used on the gradient-based image to detect all data points of the gradient-based image volume for which the gradient magnitude has a value above the first threshold value. Subsequently, a dilation of the first mask with a 3×3×3 cube and the second binary mask as a limit is performed. Thus, the data points above the second threshold value are used as starting points, whereby the value of the gradient magnitude of the data points connected to the starting points are considered. The adjacent data points having a gradient magnitude below the first threshold value are disregarded and the adjacent data points having a gradient magnitude above the first threshold value are considered.

As may be appreciated from the fifth image, this hysteresis operation results in a suppression of the data points that have been spread in between the edges in the fourth image. As a result, the fifth image is a representation of the edges only. By comparing the first and the fifth image, it becomes obvious that the data points representing with a non-zero value in the fifth image indeed correspond to the edges shown in the first image. Hence, the fifth image shows an edge-enhanced representation of the cardiac CT image. Such an edge-enhanced representation may be normalized and the subjected to the registration and motion compensated reconstruction procedure as described in relation to FIG. 1.

Figure 3:
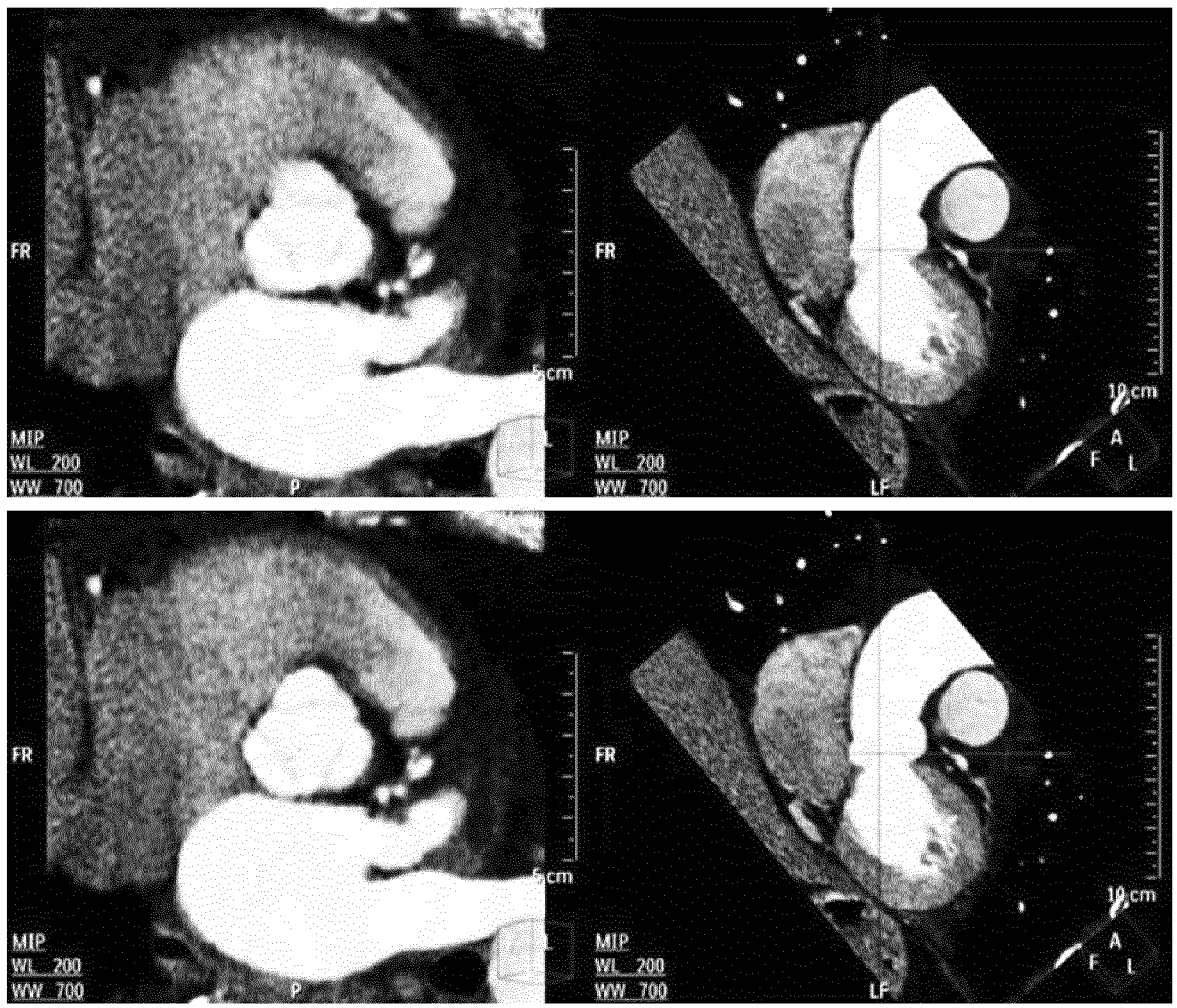
FIG. 3 is a comparative representation of two cardiac CT images of an aortic valve reconstructed using normal gated reconstruction (upper row) and reconstructed using the motion compensation reconstruction method according to the invention (lower row).

FIG. 3 shows a comparative example of two reconstructed images retrieved from CT image data for a time point corresponding to 30% cardiac phase. The two images in the upper row have been reconstructed using a normal gated reconstruction according to the prior art. The two images in the lower row have been reconstructed by means of the motion compensated reconstruction method according to the invention. As is clearly visible, in particular from the left images in the upper and lower row, the motion compensated reconstruction method according to the invention results in an improvement in quality of the image. More particularly, the visibility of the structures in the image has been improved and the blurring of the edges has been reduced.

Figure 4:
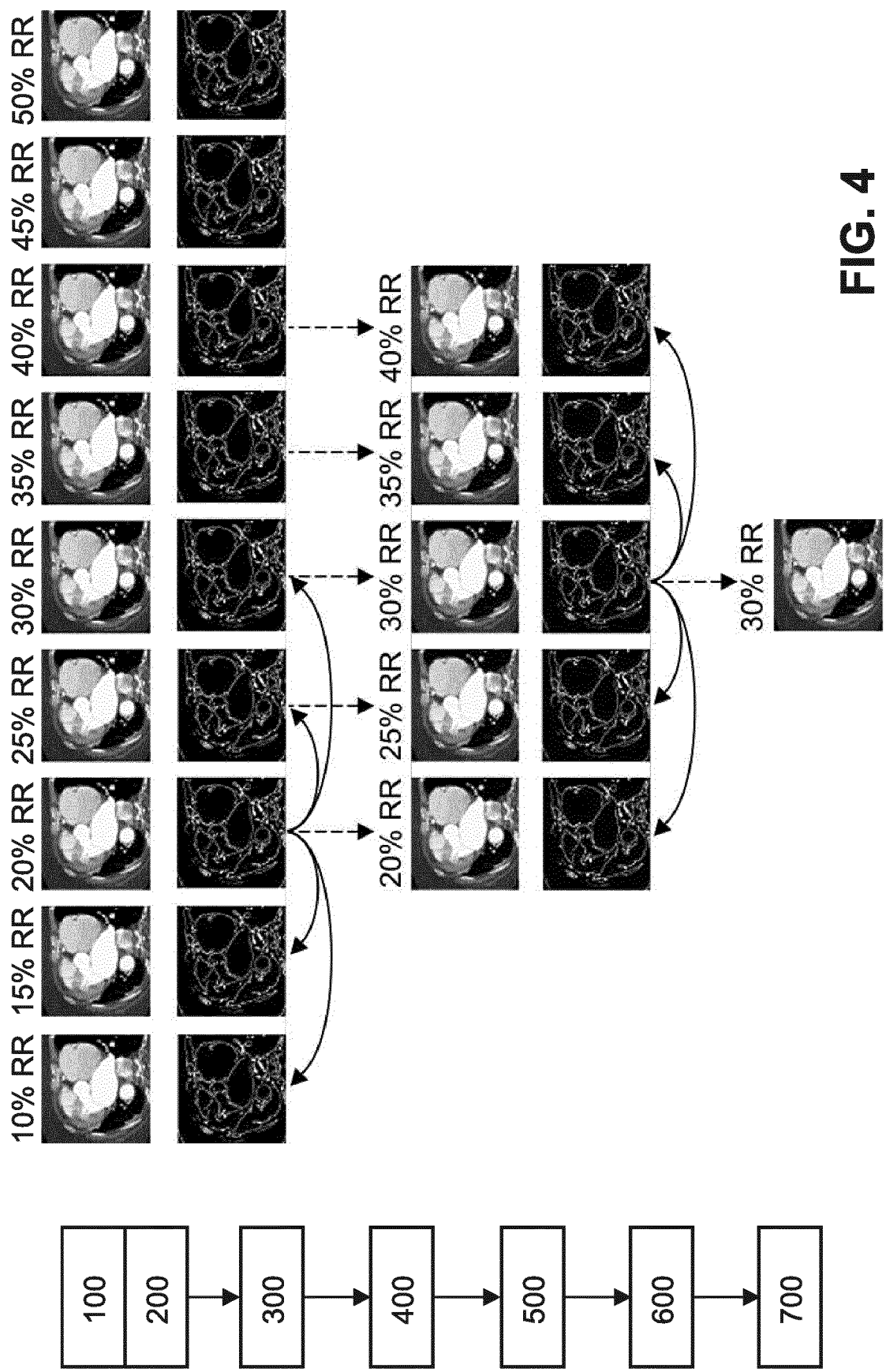
FIG. 4 schematically illustrates the method steps for second pass motion compensation for compensating valve leaflet movement.

FIG. 4 schematically illustrates the method steps for second pass motion compensation for compensating valve leaflet movement. The volumetric images correspond to a multi-phase reconstruction of cardiac CT images as shown in the upper row. These images (from left to right) have been collected at time points corresponding to 10%, 15%, 20%, 25%, 30%, 35%, 40%, 45% and 50% cardiac phase.

In step 100, each of the cardiac CT images are subjected to the gradient-based filter operation as described in relation to FIG. 1. In step 200, the thus edge-enhanced image volumes are weighted to the normalized gradient magnitude. The second-upper row thus represents the normalized results of the gradient based filter operation for the different phases between 10% to 50% cardiac phase.

In step 300, a registration procedure is performed to determine a plurality of motion vector fields. In the example according to FIG. 4, the edge-enhanced image volume determined for the time point corresponding to 20% cardiac phase is used as a first reference image volume. From this reference image volume, a respective plurality of first motion vector fields from the first reference image volume to the edge-enhanced image volumes corresponding to the time points corresponding to 10%, 15%, 25% and 30% cardiac phase are determined.

In step 400, a motion compensated filtered back projection is performed using the first motion vector fields. Based on this motion compensated filtered back projection, first motion compensated image volumes are reconstructed which are represented in the third upper row of FIG. 4. These first motion compensated image volumes correspond (from left to right) to the time points corresponding to 20%, 25%, 30%, 35% and 40% cardiac phase.

The motion compensated reconstruction is followed by a second pass motion compensation starting in step 500. Here, a line filtering operation is applied to the first motion compensated image volumes. By means of the line filtering operation each one of the first motion compensated image volumes is transferred into a corresponding line filtered image volume. These line filtered image volumes corresponding to the time points corresponding to 20%, 25%, 30%, 35% and 40% cardiac phase are shown in the fourth upper row of FIG. 4. In these line filtered image volumes, the contours of the valve leaflets, which are typically represented as lines in cardiac CT images, are enhanced.

In step 600, a registration procedure is performed on the line filtered image volumes. Hereby, the line filtered image volume corresponding to a time point corresponding to 30% cardiac phase is selected as a second reference image volume. Subsequently, a plurality of second motion vector fields from the second reference image volume to the remaining image volumes corresponding to time points corresponding to 20%, 25%, 35% and 40% cardiac phase are determined by considering the displacement of respective reference points from the second reference image volume to the remaining image volumes.

Finally, in step 700, a second motion compensated back projection is performed using the plurality of second motion vector fields. The result is the reconstruction of a plurality of second motion compensated image volumes in which the motion of the valve leaflets has also been considered. In the exemplary embodiment according to FIG. 4, the lower row represents the second motion compensated image volume corresponding to a time point corresponding to 30% cardiac phase is shown in the lower row. It shall be understood, though, that further second motion compensated image volumes may likewise be constructed.

The sequential application of a first pass motion compensation to compensate valve motion and a second pass motion compensation to compensate valve leaflet motion leads to an improved image in which less blurring is visible and the contours and shape of both, the valve and the valve leaflets may be determined with good accuracy and high visibility.

Although in above described embodiments, the images acquired are cone beam, circular or helical CT images, in other embodiments the images may also be retrieved from other kinds of computed tomography, such as phase contrast computed tomography or non-periodic computed tomography, where the scans have been performed with a small pitch (e.g. 0.7) or spectral computed tomography, whereby the energy weighting need to be adjusted to the second pass steps.

Further, the images can also be other kind of images, i.e. the gradient-based filtering and the subsequent registration and motion compensated reconstruction can also be performed if the images are not helical CT images. For instance, the images can also be images that have been acquired by a sequential CT scan, X-ray C-arm system or by images collected by other medical scanning techniques.

It is further understood that, although in the above described embodiments the aortic valve is imaged and evaluated, the motion based reconstruction method according to the invention may also be used for other parts of the heart, such as the aorta, or even other regions of the human anatomy.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Procedures like the filtering of the images, the registration of the images and the motion compensated reconstruction et cetera performed by one or several units or devices can be performed by any other number of units or devices. These procedures in accordance with the new motion compensated reconstruction method and/or the control of a CT processing device in accordance with the claimed CT method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to a method for reconstructing an image of an object of interest from a plurality of projection data of said object corresponding to a plurality of time points. The method comprises the steps of retrieving a plurality of volumetric data of the object of interest from the plurality of projection data, each one of the volumetric data corresponding to a respective time point and applying a gradient-based filter on the plurality of volumetric data to obtain a plurality of edge-enhanced image volumes corresponding to the respective time points. The method further comprises estimating a plurality of first motion vector fields on the basis of the plurality of edge-enhanced image volumes and reconstructing a plurality of first motion compensated image volumes of the object from the plurality of projection data using the estimated plurality of first motion vector fields, each of the plurality of first motion compensated image volumes corresponding to a respective time point.

The method enables an improved motion compensated reconstruction of objects of interest in the human anatomy for which the edges are typically blurred due to movement of these objects of interest.

The invention claimed is:

1. A method for reconstructing an image of an object of interest from a plurality of projection data of said object corresponding to a plurality of time points, the method comprising:
retrieving a plurality of volumetric data of the object of interest from the plurality of projection data, each one of the volumetric data corresponding to a respective time point;
applying a gradient-based filter on the plurality of volumetric data to obtain a plurality of edge-enhanced image volumes corresponding to the respective time points;
weighting of the plurality of edge-enhanced image volumes by weighting edges with a normalized gradient magnitude to obtain a plurality of normalized edge-enhanced image volumes;
estimating a plurality of first motion vector fields on the basis of the normalized plurality of edge-enhanced image volumes; and
reconstructing a plurality of first motion compensated image volumes of the object from the plurality of projection data using the estimated plurality of first motion vector fields, each of the plurality of first motion compensated image volumes corresponding to a respective time point.

2. The method according to claim 1, wherein the object of interest comprises the valves and the valve leaflets, and wherein the data corresponds to cardiac computed tomography (CT) projection data obtained together with one or more of simultaneously measured electrocardiogram (ECG) data and/or photoplethysmographic (PPG) data.

3. The method according to claim 2, wherein the time points are determined based on the ECG or PPG data, whereby the time points correspond to a cardiac phase of the heart.

4. The method according to claim 1, further comprising:
obtaining a noise-reduced image volume from the volumetric data by applying a smoothing filter;
determining a gradient and/or gradient magnitude for each of the data points of the noise-reduced image volume;
determining a plurality of local maxima of the gradient magnitude for each of the data points and suppressing the data points that do not correspond to said local maxima;
determining a first threshold value for the gradient magnitude and a second threshold value for the gradient magnitude, the first threshold value being smaller than the second threshold value;
determining, for each data point, whether the gradient magnitude is below or above the second threshold value;
determining, for each data point, whether the gradient magnitude is below or above the first threshold value;
marking a set of data points for which the gradient magnitude is above the first threshold value and which are connected to data points for which the gradient magnitude is above the second threshold value; and
obtaining, from the marked set of data points, the edge enhanced image volume.

5. The method according to claim 4, further comprising applying a Gaussian filter on the volumetric data to obtain the smoothed image volume.

6. The method according to claim 4, wherein determining the gradient for each of the data points is performed using central differences, and wherein determining the gradient magnitude for each of the data points of the smoothed image volume is performed using the Euclidean norm.

7. The method according to claim 4, wherein determining the gradient and/or the gradient magnitude for each of the data points further includes determining a direction of the gradient.

8. The method according to claim 4, wherein weighting the edge-enhanced image volume further comprises:
determining a normalized gradient magnitude; and
weighting the marked data points using the normalized gradient magnitude.

9. The method according to claim 1, wherein estimating the plurality of motion vector fields comprises:
determining a first one of the plurality of edge-enhanced image volumes as a first reference image volume; and
estimating the plurality of first motion vector fields from the first reference image volume to the remaining ones of the plurality of edge-enhanced image volumes using the first reference image volume.

10. The method according to claim 1, further comprising:
obtaining a plurality of line filtered image volumes from the plurality of first motion compensated image volumes;
estimating a plurality of second motion vector fields based on the plurality of line filtered image volumes; and
reconstructing a plurality of second motion compensated image volumes of the object from the projection data using the estimated plurality of second motion vector fields.

11. The method according to claim 1, wherein obtaining the plurality of line filtered image volumes comprises:
determining a registration transformation for registering a first one of the first motion compensated image volumes to each of the remaining ones of the plurality of first motion compensated image volumes; and
obtaining the plurality of line filtered image volumes from the plurality of registered first motion compensated image volumes.

12. The method according to claim 1, further comprising selecting a region of interest within the volumetric data.

13. An image processing device for reconstructing an image of an object of interest from a plurality of projection data of said object corresponding to a plurality of time points, comprising:
a memory configured to store a plurality of volumetric data of the object of interest retrieved from the plurality of projection data, each one of the volumetric data corresponding to a respective time point;
at least one processor configured to:
apply a gradient-based filter on the plurality of volumetric data to obtain a plurality of edge-enhanced image volumes corresponding to the respective time points;
estimate a plurality of first motion vector fields based on a plurality of normalized edge-enhanced image volumes obtained by weighting the plurality of edge-enhanced image volumes by weighting edges with a normalized gradient magnitude; and
reconstruct a plurality of first motion compensated image volumes of the object from the plurality of projection data using the estimated plurality of first motion vector fields, each of the plurality of first motion compensated image volumes corresponding to a respective time point.

14. A non-transitory computer-readable medium having one or more executable instructions stored thereon which, when executed by at least one processor, cause the at least one processor to perform a method for reconstructing an image of an object of interest from a plurality of projection data of said object corresponding to a plurality of time points, the method comprising:

retrieving a plurality of volumetric data of the object of interest from the plurality of projection data, each one of the volumetric data corresponding to a respective time point;

applying a gradient-based filter on the plurality of volumetric data to obtain a plurality of edge-enhanced image volumes corresponding to the respective time points;

weighting the plurality of edge-enhanced image volumes by weighting edges with a normalized gradient magnitude to obtain a plurality of normalized edge-enhanced image volumes;

estimating a plurality of first motion vector fields on the basis of the normalized plurality of edge-enhanced image volumes; and reconstructing a plurality of first motion compensated image volumes of the object from the plurality of projection data using the estimated plurality of first motion vector fields, each of the plurality of first motion compensated image volumes corresponding to a respective time point.

* * * * *